United States Patent [19]
Edberg

[11] Patent Number: 4,925,789
[45] Date of Patent: May 15, 1990

[54] METHOD AND MEDIUM FOR USE IN DETECTING TARGET MICROBES IN SITU IN A SPECIMEN SAMPLE OF A POSSIBLY CONTAMINATED MATERIAL

[76] Inventor: Stephen C. Edberg, 356 Woodland La., Orange, Conn. 06477

[21] Appl. No.: 880,305

[22] Filed: Jun. 30, 1986

[51] Int. Cl.$^5$ .......................... C12Q 1/10; C12Q 1/08; C12Q 1/06; C12Q 1/04
[52] U.S. Cl. ....................................... 435/38; 435/34; 435/39; 435/40; 435/252.8; 435/253.6
[58] Field of Search ...................... 435/34, 31, 32, 243, 435/244, 253, 36, 38, 39, 253.6, 40, 252.8, 252.4

[56] References Cited

U.S. PATENT DOCUMENTS

| 4,208,480 | 6/1980 | D'Amato et al. | 435/34 |
| 4,245,043 | 1/1981 | Lund | 435/34 X |
| 4,591,554 | 5/1986 | Koumura et al. | 435/38 X |
| 4,622,297 | 11/1986 | Kappner et al. | 435/32 |
| 4,675,289 | 6/1987 | Kanou et al. | 435/34 X |
| 4,803,162 | 2/1989 | Smith et al. | 435/34 X |
| 4,812,409 | 3/1989 | Babb et al. | 435/38 X |

FOREIGN PATENT DOCUMENTS

| 0025467 | 3/1981 | European Pat. Off. . |
| 0059645 | 9/1982 | European Pat. Off. . |
| 2005410 | 4/1979 | United Kingdom . |

OTHER PUBLICATIONS

Dahlen et al., Applied Microbiology, vol. 26, No. 6, Dec. 1973, pp. 863–866.
Maddocks et al., Journal of Clinical Pathology, vol. 28, 1975, pp. 686–687.
Hansen et al., Journal of Clinical Microbiology, vol. 20, No. 6, Dec. 1984, pp. 1177–1179.

Primary Examiner—Randall E. Deck
Attorney, Agent, or Firm—William W. Jones

[57] ABSTRACT

The presence or absence of a predetermined target microbe in a sample is determined by adding a testing medium to the sample, or vice versa. The testing medium provides a selective growth medium for the target microbe and includes a specific nutrient which only the target microbe can metabolize. This specific nutrient is modified by attaching a sample-altering moiety thereto, thereby converting the nutrient to a nutrient-indicator. The sample-altering moiety is activated to alter the sample only if the specific nutrient is metabolized by the target microbe. The sample-altering moiety can be a material which changes the color of the sample (visible or non-visible) or changes an electrical characteristic of the sample, or alters some other detectable characteristic of the sample. The testing media does not have to be kept sterile, and the testing procedure does not have to be performed in a sterile environment.

19 Claims, No Drawings

METHOD AND MEDIUM FOR USE IN DETECTING TARGET MICROBES IN SITU IN A SPECIMEN SAMPLE OF A POSSIBLY CONTAMINATED MATERIAL

This invention relates to the detection of microbes in a sample such as water, food, or the like. More particularly, this invention relates to the detection of a target microbe through the use of a not necessarily sterile testing medium which contains a nutrient which can be significantly metabolized only by the target microbe and which, once metabolized, releases a moiety which alters a characteristic of the sample. The medium is thus a "specific medium" in that it will support growth of only the target microbes rather than a general medium which will also support growth of microbes other than the target microbe.

In order to detect microbial pathogens in specimens, whether of human, animal or environmental origin, the following general procedure is commonly used: the target (and other) microbes in the specimen are inoculated with the specimen into a culture medium in which they are provided with all the nutrients they require for growth. The specimen may be an untreated natural sample, or it may be a sample which has been pretreated as, for example, by membrane filtration. The culture medium has the nutrients and other selective chemicals such as antimetabolites or antibiotics, which are selectively active against microbes other than the target microbes. The culture medium is a "general medium," even with the selective chemicals, in that it supports the growth of both target microbes and related microbes and thus is only partially specific to the target microbes.

The culture medium, which may be a water solution or a water gel, is sterilized to rid it of any contaminating microbes which may be present and which could, therefore, interfere with the analysis. The culture medium must be refrigerated and packaged in such a way to avoid contamination after manufacture.

After one or more of the culture media are inoculated with the specimen, the inoculated media are incubated for at least sixteen to eighteen hours or longer under controlled atmospheric conditions. After incubation, the culture media are examined for growth compatible with the target microbe. If such growth is observed, a sample thereof is taken for further analysis, since the presence of the target microbe can only be established by isolating it in the pure state, not mixed with other microbes. Once isolated on subsequent culture media, the target microbes are identified by testing for a variety of physical and chemical characteristics. If the apparent target microbe growths are not isolated, false negative tests can result.

It will be readily appreciated that this most common analytical procedure is time consuming and must be carefully performed to preserve sterility.

One area where considerable effort has been made to simplify and speed up the testing procedures is in the testing of water for microbes. The following are examples of such efforts.

Manja devised a field test for the detection of fecal pollution of drinking water by the analysis of hydrogen sulfide directly from a reaction broth. This test has not yet experienced widespread use because it is most conducive for the isolation of Salmonella and does not select *Escherichia coli* (*E. coli*). Smith developed a rapid single tube confirmatory test for *E. coli*. He modified lauryl tryptose by halving the amount of lactose and adding 10% tryptophane. Reasoner developed a rapid seven-hour fecal coliform test based on the membrane filtration procedure. After the 100 ml sample is filtered through a membrane, it is placed on a medium called m-7 and incubated at 44.5° C. for seven hours. Fecal coliforms are yellow, indicating lactose fermentation. Although the technique is rapid, it is not amenable to field work and suffers from the same lack of specificity as the MPN (most probable number) procedure.

Several investigators have attempted to detect bacterial by-products as a means of analysis of water supplies. Jorgensen utilized a Limulus lysate assay to detect bacterial endotoxins. The presence of bacteria have also been determined by electrical impedance measurements, ATP assays, and the Carbon 14 labeled substrate assay. None of these tests, however, has been accepted in the field because they do not specifically analyze microbes associated with an intracolonic existence and which can be utilized as sentinel bacteria to predict the presence of gastrointestinal pathogens.

There are indicators of microbial growth that change color only after the microbe grows. They do not participate, however, as a foodstuff for the microbe. They are accessory to the chemicals that provide sustinence to the target microbes. They participate solely by reacting chemically with a metabolic by-product produced by the target microbes. They do not exert any stimulatory effect on the target microbes. Chemicals that change color when pH changes have been used to mark the presence or absence of bacterial growth. Commonly utilized pH indicators include phenol red, bromocresol blue, and neutral red. In order to use these indicators, the medium in which the microbe grows has to be complete. Sources of carbon, amino acids, salts, vitamins, fatty acids, and energy are required. The indicator is an accessory substance. In the terminology of Microbiology, the medium is general to numerous microbes, in that it will support the growth of numerous microbes, with an indicator added.

Attempts have been made to measure bacterial growth using other than pH indicators. Markers, such as electrical impedance, electrical conductivity, amount of ATP (adenosine triphosphate), turbidity (optical density), have been measured from microbes growing in a general medium with the addition of a chemical that is measured. For example, Golber (U.S. Pat. No. 3,206,317) utilizes triphenyl tetrazolium chloride in a medium containing protein, yeast extract, dextrose, sodium chloride, and sources of other nutrients. He further describes in the same patent a general medium with a pH indicator, phenol red. A sample thought to contain the target microbe(s) is inoculated into the medium. The medium contains all the constituents necessary for growth, metabolism, and multiplication of not only the target microbes but other microbes as well. After the microbes grow, they metabolize one or more constituents in the medium. The microbes, after metabolizing, eliminate waste and other products. The waste and other products can be measured by the reaction with the indicator. For example, one class of waste product from microbes is ionic hydrogen, which creates an acid condition and changes phenol red from red to yellow. Other waste products are reducing agents. These will react with tetrazolium chloride to convert this dye from colorless to blue-purple.

Berger et al (U.S. Pat. No. 3,496,066) describes the use of a novel series of compounds that bacteria convert from precursors to dyestuffs. They disclose that different bacteria can convert different precursors to different colored dyestuffs. In each case, the precursors do not serve as a foodstuff for the bacteria. After the microbes metabolize, grow, and multiply in general media, the precursors are converted to dyestuffs.

Bochner (U.S. Pat. No. 4,129,483) describes a means of identifying or testing for a microbe by the change of an oxidation-reduction indicator. The microbe catabolizes the oxidation-reduction indicator, a tetrazolium compound, that undergoes a change in color. A requirement for the invention is the inclusion in the medium of a nutrient that will support the growth of the microorganism without itself affecting the indicator. Bochner requires that the indicator in his invention be a non-biodegradable compound and participate by changing color after being reduced.

This invention detects target microbes in a sample by using an indicator which is the preferred or primary nutrient for the target microbe but cannot be substantially metabolized by any other viable microbes which may be present in the sample along with the target microbe. The invention thus uses an active selector of the target microbes, rather than the passive reactors used by the prior art. The indicator will change a characteristic of the sample once the nutrient is metabolized by the target microbe. The characteristic can be: color (either visible, ultra violet, or infrared); electrical conductivity; electrical impedance; or the like. The preferred mode of performing the invention involves detecting the target microbes by use of a nutrient-indicator which, when metabolized, changes the visible or fluorescent color of an aqueous solution containing the specimen.

The nutrient-indicator actively participates in the growth of the target microbes by serving as the preferred or primary nutrient source. The target microbes can grow, metabolize, and multiply because they, and substantially only they, can use the indicator as their primary nutrient. Indicators can include chromogens attached to: salts; carbon; nitrogen; sulfur; amino acids; fatty acids; peptides; or other selective primary nutrients for microbes. Because microbes other than the target microbes are prevented from growing, metabolizing, or multiplying, the media is so specific that the invention does not have to be sterilized before use. Competition between target microbes and other microbes for the available nutrients in the media is eliminated by the subject invention. The medium can be manufactured and packaged in a powder form which is added to the sample being tested. As noted, no sterilization is necessary. The medium can be dissolved in water and the sample can be added to the solution, or, if the sample is aqueous, the medium can be added directly to the sample. There is no need for a minimum incubation time to ensure growth of the target microbe since no other microbes in the sample will be able to substantially metabolize the nutrient in the media.

The development of a specific color indicates the presence of the target microbes. This may occur at any time after the procedure is initiated. There is no need to purify the target microbes. There is no need to perform any chemical analysis of the sample to determine whether the target microbe is present.

The naming of microbes is a science called taxonomy. One starts with certain gross characteristics and works his way down a decision tree. The further one goes down the decision tree, the more specific the characteristics are to place a given microbe at that level. Each level has its own name such as kingdom, tribe, family, etc. Genus and species are the last two levels on the decision tree. It is by the genus and species name that microbes are known.

Microbes, like human beings, have two names to describe their place in the scientific world. They are the genus name and the species name. The genus refers to a group of microbes that share characteristics in common. By analogy, it is similar to a human's family name. The species is the classification that cannot be further subdivided. It is similar to the human's first name. Like human names, however, microbes having the same genus and species name (e.g., *Escherichia coli*) may not be all identical. The genus name comes before the species name (similar to last name first).

As used in this disclosure, the term "target microbes" can refer to a single microbe, a related species of microbes, or a large genus of microbes possessing a common taxonomic characteristic. The indicator only needs to be specific to the "target microbe." For example, indicators are available for detecting a single microbe, such as *Escherichia coli* (*E. coli*), or for detecting any one of a closely related species of microbes, such as Klebsiella - Enterobacter - Serratia, or any one of a large genus of microbes, such as Gram negative bacteria. The chromogens used in the nutrient-indicator can produce color in the visible range, the ultraviolet range, or the infrared range. As will be appreciated from the aforesaid, the nutrient-indicator will preferably be colorless in the non-metabolized state, and will preferably release a color moiety after being metabolized by the microbes. The color may be visible, fluorescent, or machine-readable. As previously noted, using the invention, there is very little or no competition for food or nutrient among the microbes in the media because the only nutrient present in the media can be metabolized to any significant extent solely by the target microbes. Accordingly, a significant number of false-negative tests which will occur with the procedures of the prior art are eliminated by this invention. The nutrient used will be one that the target microbes greatly prefer over any other nutrients, and also, one to which other microbes have little or no preference. Thus, only the presence of the target microbes in the specimen can result in sufficient metabolism of the nutrient to cause the color or other characteristic change in the sample.

Since the nutrient-indicator is specific substantially only to the target microbe, and is the preferred or primary nutrient in the media for the target microbe, the target microbe will be drawn to the nutrient-indicator, thus speeding up the color change.

It is, therefore, an object of this invention to provide a procedure for detecting microbes in a specimen by metabolistically changing a detectable characteristic of the sample.

It is an additional object of this invention to provide a procedure of the character described wherein the color of the sample is changed by metabolization of a target microbe.

It is another object of this invention to provide a procedure of the character described wherein the color change is provided by metabolism of a nutrient added to the sample, which nutrient includes a chromogenic moiety which is detectable only after the nutrient is metabolized.

It is a further object of this invention to provide a procedure of the character described wherein the nutrient having the chromogenic moiety can only be significantly metabolized by the target microbe.

These and other objects of the invention will become more readily apparent from the following detailed description of several preferred embodiments of the invention.

Three examples of the use of the invention to detect a genus and a species of gram negative microbe (*Escherichia coli*), a genus and species of gram positive microbe (*Streptococcus faecalis*), and a taxomonic class consisting of a large group containing many members (gram negative microbes) are set forth hereinafter. When a specimen is examined for any of these three, each is referred to as the target microbe(s).

Escherichia coli

The nutrient is a substrate for the enzyme B-glucuronidase. If one wishes to determine the presence of *E. coli* by a color change, the nutrient-indicator can be orthonitrophenyl-B-D-glucuronide (yellow), B-napthalamide-B-D-glucuronide (purple), alpha-napthol-B-D-glucuronide (red), or methylumbilliferyl-B-D-glucuronide (fluorescent), or the like.

The nutrient-indicator serves as the essential source of carbon. The rest of the medium is tailored so that each ingredient provides a requirement for *E. coli*.

First, to prevent competition from microbes other than the broad category of gram negative bacteria, the antibiotics vancomycin and ansiomycin are added in the percent by weight of 5%. These antibiotics may be present in the range of 1% to 10% by weight.

Second, to select *E. coli* from gram negative bacteria, the following ingredients are used:

| INGREDIENT | SOURCE | Preferred % by Weight | Range % by Weight |
|---|---|---|---|
| Nitrogen | ammonium sulfate | 37. | 10–50 |
| Amino Acids | histidine | .0697 | 0.02–0.1 |
|  | methionine | .1860 | 0.02–0.4 |
|  | tryptophan | .2325 | 0.02–0.5 |
| Vitamins | biotin | .000232 | 0.0001–0.001 |
|  | pantothenate | .0093 | 0.001–0.03 |
|  | folic acid | .000232 | 0.0001–0.02 |
|  | inositol | .0186 | 0.01–0.02 |
|  | p-aminobenzoic acid | .046 | 0.01–0.1 |
|  | pyridoxine hydrochloride | .093 | 0.05–0.3 |
|  | riboflavin | .037 | 0.01–0.06 |
|  | thiamine | .037 | 0.01–0.06 |
| Elements | ferric chloride | .046 | 0.02–0.1 |
|  | copper sulfate | .001860 | 0.001–0.002 |
|  | manganese sulfate | .0037 | 0.002–0.007 |
|  | potassium chloride | .0000009 | 0.00001–0.001 |
|  | potassium iodide | .0000046 | 0.000001–0.00001 |
|  | zinc sulfate | .046 | 0.01–0.08 |
|  | boric acid | .460 | 0.01–0.5 |
|  | magnesium chloride | .019 | 0.01–0.05 |
| Salts | potassium phosphate monobasic | 9.0 | 1–15 |
|  | potassium phosphate dibasic | 23.0 | 2–30 |
|  | sodium carbonate | 23.0 | 2–30 |
|  | magnesium sulfate | 4.6 | 1–10 |
|  | sodium chloride | .9 | 0.2–5 |
|  | calcium chloride | .9 | 0.2–5 |
|  | sodium pyruvate | .023 | 0.01–0.1 |
| Nutrient-Indicator |  | .345 | 0.2–2 |

Streptococcus faecalis

*Streptococcus faecalis* is a microbe found as a cause of urinary tract infection. It is also the major bacterium analyzed in swimming water.

The nutrient-indicator is a substrate of the enzyme L-pyronidonyl aminopeptidase. If one wishes to determine the presence of *S. faecalis* by a color change, the nutrient-indicator molecule can be orthonitrophenyl-B-L-pyronidonyl (yellow), B-napthalamide-B-L-pyronidonyl (purple), alpha-napthol-B-L-pyronidonyl (red), and methylumbilliferyl-B-L-pyronidonyl (fluorescent).

The nutrient-indicator serves as the essential source of carbon. The rest of the medium is tailored so that each ingredient provides a requirement for *S. faecalis*.

First, to prevent competition from microbes other than the broad category of gram positive bacteria, the antibiotics colistin, naladixic acid and ansiomycin are added.

Second, to select *S. faecalis* from gram positive bacteria, the same ingredient mixture specified for *E. coli* is used with the above-noted nutrient-indicator and antibiotics. The nutrient-indicator is present in a concentration of 0.345 percent by weight, the usable range being about 0.2 to about 2.0 percent by weight and the antibiotics are present in the concentration of 5 percent by weight, the usable range being about 1 to about 10 percent by weight.

GRAM NEGATIVE BACTERIA

There are two broad classes of bacteria; gram positive and gram negative. Gram negative bacteria are important because they contain a toxic material as part of their bodies called endotoxin. They also may contaminate pharmaceuticals and other medical preparations.

The nutrient-indicator is a substrate of the enzyme L-alanine aminopeptidase. If one wishes to determine the presence of gram negative bacteria by a color change, the nutrient-indicator molecule can be L-alanine-B-orthonitrophenyl (yellow), beta-napthalamide-B-L-alanine (purple), alpha-napthol-B-L-alanine (red), and methylumbilliferyl-B-L-alanine (fluorescent).

The nutrient-indicator serves as the essential source of carbon. The rest of the medium is tailored so that each ingredient provides a requirement for gram negative bacteria.

First, to eliminate microbes other than the broad category of gram negative bacteria, the antibiotics ansiomycin (eliminates yeast) and vancomycin (eliminates gram positives) are added in amounts of 5 percent by weight.

The same ingredient mixture specified above is used with the nutrient-indicator being present in the amount of 0.345 percent by weight and in the range of about 0.2 to about 2.0 percent by weight, and the antibiotics may be present in the range of about 1 to about 10 percent by weight.

Additional Examples

A primary carbon source can be used as the primary nutrient in the detection of the family Klebsiellae in water. The bacteria in the family Klebsiellae can metabolize carbon sources in which the carbon in sugar molecules are attached by B-D linkages. A detection formulation for this species includes as the primary carbon nutrient source, a glucose molecule attached through the B-D linkage to orthonitrophenyl, a chromogenic moiety, and the antibiotics colistin and naladixic acid. A specimen is inoculated with the detection formulation. If the family Klebsiellae is present, the orthonitrophenyl-B-D-glucose will be metabolized with the release of the orthonitrophenyl moiety. This moiety, when released, becomes yellow. Therefore, the yellow color in the specimen indicates the presence of the target microbes, i.e., the family Klebsiellae. Other microbes will not grow because they cannot metabolize the indicator, orthonitrophenyl-B-D-glucose. There will not be microbial competition with other microbes, because they will not grow and metabolize.

*Staphylococcus aureus* can be identified in the presence of other Staphylococci in a mixed water sample because this target microbe can metabolize $PO_4$. Orthonitrophenyl attached to phosphate can be used as a metabolizable indicator in the testing medium to detect this species. After the sample containing the mixture is admixed with the medium, only *Staphylococcus aureus* will metabolize the nutrient in the medium and release the indicator, causing a yellow color to be observed. Gram negative bacterium and yeast are eliminated from the specimen by addition of colistin, naladixic acid and ansiomycin respectively.

Nitrogen and sulfur are metabolized by microbes principally in their reduced forms as amino groups or ammonia salt ($NH_3$) and sulfhydryl (SH) groups. Like carbon, nitrogen and sulfur are absolutely required for growth. This invention utilizes the same principle described for carbon in synthesizing tests that utilize hydrolyzable substrates linked to nitrogen or sulfur to detect and enumerate microbes.

An example is the detection of *Mycobacterium fortuitum*. This bacterium requires as its source of sulfur, the sulfate ion, $SO_4$. The nutrient-indicator phenolphthalein-sulfate is normally colorless. In a medium with all constituents required for growth, except a source of sulfur, only *Mycobacterium fortuitum* of the genus Mycobacterium can utilize sulfate. Therefore, only this species will grow and metabolize. Its presence will be demonstrated by the red color produced by the released chromogenic moiety phenolphthalein.

Another example of the use of a nutrient which can be converted to a nutrient-indicator is the compound triglycerideorthonitrophenyl. The genus Fusobacterium is the only gram negative anaerobic bacterium of medical importance that utilizes triglyceride in order to grow and metabolize. If a sample containing Fusobacterium is inoculated in an anaerobic medium containing all growth requirements and triglyceride-orthonitrophenyl as the primary source of triglyceride, only Fusobacterium will metabolize. Its metabolism will be demonstrated by the yellow color produced by the release of the moiety orthonitrophenyl.

This invention is tailored to the individual, species or genus of target microbes by choosing a nutrient-indicator that only the target microbes can use as a primary nutrient to replace a general nutrient in the medium. Thus, the medium is a specific and not a general medium.

*E. coli* cannot metabolize the sugar adonitol, whereas *Klebsiella pneumoniae* (*K. pneumoniae*) can. Therefore, *E. coli* will not grow, metabolize, and multiply if adonitol is the only nutrient in the medium, and *K. pneumoniae* will. A medium can be created based on this fact by providing all growth factors *K. pneumoniae* requires with adonitol being the primary nutrient whereby *K. pneumoniae* will metabolize and grow. If *E. coli*, a related bacterium, is present in the same medium, it will not metabolize and grow. Therefore, a chromogenic moiety attached to adonitol will serve as a nutrient-indicator to detect the growth and metabolism of *K. pneumoniae* in the presence of a specimen mixed with *E. coli*.

The nutrient-indicators are artificial molecules that have never before been used as primary nutrients. Like the adonitol example, a particular nutrient-chromogen will be attacked by the target microbe and release a colored moiety. Because other microbes cannot metabolize it, they will not grow.

A sample of the specimen is added to a vessel, such as a bottle. The invention is added to the specimen and well mixed. If the sample is a solid, a water diluent can be used. If the target microbe or group of microbes are present, the invention will change color (at any time from the time of inoculation). There is no technical time or labor required after inoculation of the invention. Also, because the end-point is a defined color change, it does not require a trained individual to determine positivity.

Substrates are available to specifically detect fecal coliforms (*E. coli*), total coliforms, the Klebsiella-EnterobacterSerratia group, and *Streptococcus faecalis*.

This invention is particularly useful in analyzing water. When water is analyzed, if necessary, sodium thiosulfate or sodium EDTA may be added to neutralize antibacterials found in water.

To analyze water for *E. coli* by the invention, the following procedure is followed:

1. A water sample is collected. Using a precalibrated pipette, 1.0 milliliter, 0.1 milliliter, and 0.01 milliliter are added to each of three tubes. The aforesaid medium of this invention is added in powder form (alternatively, the invention can be present in powder form in the tubes).

2. The tubes are incubated at between 20° C. (70° F.) to 44° C. (140° F.).

3 The presence of *E. coli* is indicated by the change in color of the tube.

4. If greater than 100 *E. coli*/ml are present, the 0.01 tube will be positive; if greater than 10 *E. coli*/ml are present, the 0.1 ml tube will be positive; if less than one *E. coli*/ml is present, only the 1 ml tube will be positive.

A positive test can occur anytime from shortly after inoculation with a heavily inoculated sample to 20 hours if there is one bacterium present per milliliter of sample. The only technical manipulation is the addition of the water to the tubes by pre-calibrated pipettes.

The same medium described above was used to analyze water in the presence or absence (P-A) test for *E. coli*.

1. A 100 ml sample of water is added to a vessel containing the aforesaid medium of this invention.

2. When the reaction mixture changes color (a maximum of 18 hours), *E. coli* is present and the test is positive.

3. Confirmatory or other tests are not necessary.

The procedure of this invention was tested with several B-glucuronidase and B-galactopyranoside substrates in the field. A comparison of the procedure of this invention in a P-A test format was made with the conventional membrane filtration technique and analyzed according to the EPA protocol for the certification of new devices. The procedure of this invention is specific and requires no confirmatory tests. The test was conducted for two target microbes; *E. coli* and total coliforms. The base formula was made as described above; only the hydrolyzable substrate was changed for the detection of the particular target microbes.

The following relates to the rapid autoanalysis formulation format.

The autoanalysis formulation was made with several substrates for B-glucuronidase and B-galactosidase and tested in the field. The B-glucuronidase substrate is for *E. coli*; the B-galactosidase formulation is for total coliforms; the two substrates together will identify both microbes simultaneously. Comparison of the autoanalysis formulation in the P-A test format was made with the membrane filtration technique.

The autoanalysis formulation was made for two types of target microbe(s): *E. coli* and total coliforms. Different substrates for B-glucuronidase (*E. coli*) and B-galactosidase (total coliforms) were tested. The substrates were varied according to the color producing (chromogenic) portions of the molecule.

Substrates for B-glucuronidase (1) The following substrates for B-glucuronidase were tested separately for their ability to detect *E. coli*:
orthonitrophenyl-glucuronide: becomes yellow when hydrolyzed.
methylumbelliferone-glucuronide: becomes fluorescent at 366 nm when hydrolyzed.
bromo-chloro-indole-glucuronide: becomes blue when hydrolyzed.

(2) The following substrates for B-galactosidase were tested separately for their ability to detect total coliforms.
orthonitrophenyl galactoside: becomes yellow when hydrolyzed.
methylumbelliferone-galactoside: becomes fluorescent at 366 nm when hydrolyzed.

(3) The following combinations were tested for their ability to determine simultaneously the presence of *E. coli* and/or total coliforms:
methylumbelliferone-glucoside + orthonitrophenyl-galactopyranoside: if *E. coli* ( fecal coliforms) is present, the test solution becomes fluorescent at 366 nm; if total coliforms are present it becomes yellow; if both types of coliforms are present, the solution becomes fluorescent and yellow.
bromo-chloro-indole-B-glucoside to detect *E. coli* (fecal coliforms) + methylumbellifone-galactopyranoside to detect total coliforms: if *E. coli* (fecal coliforms) is present, the test solution becomes blue; if total coliforms are present, it becomes yellow; if both are present the solution becomes both blue and fluorescent.

Base Media Tested (1) The following basal formulae were employed:
chromogenic substrates in autoanalysis formulation.
chromogenic substrates in lauryl lactose tryptose broth.

Results (1) Assay for the presence of *E. coli* by the use of methylumbelliferone glucuronide in lauryl lactose tryptose broth.

75 specimens of raw, untreated water from a reservoir lake were tested. The membrane filtration technique gave 12 positive results for total coliforms and 12 for fecal coliforms. The lauryl lactose tryptose broth that contained the indicator detected 6 cases of total coliforms and 2 cases of *E. coli*. The average identification time was 16.5 hours. The endpoints were difficult to determine because of turbidity and lactose fermentation caused by bacteria other than coliforms. The use of lauryl lactose as the base was discontinued and this medium not further investigated.

(2) Assay for the presence of *E. coli* (fecal coliforms) by the use of orthonitrophenyl-galactoside in autoanalysis formulation to test.

35 specimens of raw, untreated water from a reservoir lake were tested. The membrane filtration and autoanalysis method each obtained one positive result. The average identification time was 18 hours.

(3) Methylumbelliferone-B-glucuronide substrate for *E. coli* (fecal coliforms) + orthonitrophenyl-B-galactopyranoside for total coliforms, assayed simultaneously.

80 specimens of raw, untreated water from a reservoir lake were tested. The membrane filtration technique obtained zero positive results for fecal coliforms and eight for total coliforms. The autoanalysis formulation detected zero *E. coli* and eight positive cases of total coliforms. The average time of the detection was 18 hours.

(4) Bromo-chloro-indole-B-D-glucuronide for *E. coli* (fecal coliforms) + methylumbelliferone-galactopyranoside for total coliforms, assayed simultaneously.

10 specimens of raw, untreated water from a reservoir lake were tested. The membrane filtration technique gave one positive result for total coliforms. The autoanalytical formulation detected one positive result for total coliforms in the same sample. The average time of identification was 22 hours.

(5) Orthonitrophenyl-B-galactopyranoside for total coliforms.

50 specimens of finished water from the distribution system were tested. The membrane filtration technique gave two positive results for total coliforms (< 2 CFU/100 mL). The autoanalysis formulation detected the same two total coliforms. The average time of detection was 17 hours.

(6) Methylumbelliferone-B-galactoside for total coliforms.

20 specimens of finished water from the distribution system were tested. The membrane filtration and autoanalysis formulation technique both obtained one total and the same positive case of total coliforms. The average time of identification was 18 hours.

(7) Methylumbelliferone-B-glucuronide for *E. coli* (fecal coliforms) + bromo-chloro-indole-B-galactoside for total coliforms assayed simultaneously.

50 specimens of raw, untreated water from a lake reservoir were tested. The membrane filtration technique gave 16 positive results for total coliforms and two for *E. coli*. The formulation detected the same 16 plus two additional cases of total coliforms and two cases of *E. coli*. The average time of identification was 18 hours.

Nutrient-indicators useful in connection with this invention may be produced as follows:

Orthonitrophenyl Derivatives

The reaction mixture is: 42 g of 0-nitrophenyl are dissolved in 420 ml of distilled water containing 16.8 g of NaOH. To this solution tetracetyl-B-D-galactopyranosyl bromide in 620 ml of acetone is added. After reaction at room temperature for five hours, the solvent is removed by evacuation. One gram or this reactant is suspended into 50 ml of methanol containing of 0.4 N barium methoxide. Crystals forming from this reaction were 0-nitrophenyl-B-D-galactopyranoside.

Paranitrophenylsulfatase

The following reaction is made: 47 ml of dimethylanaline and 50 ml carbon disulfide are mixed and cooled to 4° C., 9.2 ml of chlorsulfonic acid are added and 13.9 g of p-nitrophenol are added and mixed and allowed to stand overnight. Potassium hydroxide, 0.4N 100 ml, is added. Bright yellow crystals are captured by heating the mixture at 80° C. with carbon disulfide being evaporated. Excess methylanaline is separated by centrifugation. The substrate, p nitrophenyl, is recrystallized from alcohol.

It will be readily appreciated that the specific medium of this invention can be produced in powder form and packaged in ready-to-use quantities specific to a variety of target microbes. The medium as produced can include antibiotic components, if desired.

Since many changes and variations of the disclosed embodiments of this invention may be used without departing from the inventive concept, it is not intended to limit the invention otherwise than as required by the appended claims.

What is claimed is:

1. A specific medium for combination with a specimen sample of a material suspected to be contaminated to determine the presence of absence of a target microbe in the specimen sample, and which can detect the presence of said target microbe without the need of performing a preliminary target microbe growth step, said medium comprising operative amounts of essential vitamins and elements needed to support growth of said target microbe and a nutrient-indicator which is the primary nutrient in the medium and which is substantially the only nutrient in said medium which can be metabolized by said target microbe to the extent needed to support continued reproductive growth thereof, and which cannot be metabolized by other viable microbes in the specimen, to that extent, said nutrient-indicator including a metabolizable moiety and a sample-altering moiety, the latter of which is released only when said nutrient-indicator is metabolized by said target microbe, whereupon a sensible characteristic of the sample is altered.

2. The medium of claim 1 further comprising an effective amount of antibiotic material to render any competing non-target microbes which may be present in the sample unable to metabolize said nutrient-indicator, said antibiotic material being ineffective against said target microbe.

3. The medium of claim 1, wherein said sample-altering moiety is a chromogen which, when released by metabolization of the nutrient-indicator, will alter the color of the specimen sample.

4. A specific medium for addition to a specimen sample of a material suspected to be contaminated with *E. coli* to determine the presence or absence of *E. coli* in the specimen sample, and which can detect the presence of *E. coli* without the need of performing a preliminary *E. coli* growth step, said medium comprising operative amounts of essential vitamins and elements needed to support growth of *E. coli* and a chromogenic substrate for β-glucuronidase enzyme which is substantially the sole carbon source nutrient in the medium and which is metabolizable by *E. coli* to the extend needed to support continued reproductive growth thereof, and which, when metabolized, releases a chromogen which alters the color of the specimen there being no other nutrients in the medium which are able to support substantial reproductive growth of *E. coli* in the sample.

5. The medium of claim 4 wherein said chromogenic substrate of B-glucuronidase is a glucuronide selected from the group consisting of orthonitrophenyl-B-D-glucuronide, B-naphthalamide-B-D-glucuronide, alpha-napthol-B-D-glucuronide, methylumbilliferyl-B-D-glucuronide, bromo-chloro-indole-B-D-glucuronide, and mixtures thereof.

6. The medium of claim 4 further comprising an effective amount of antibiotic material operable to render any competing microbes incapable of metabolizing said chromogenic substrate.

7. The medium of claim 6 wherein said antibiotic material is selectively operable against gram positive bacteria.

8. A specific medium for addition to a specimen sample of a material suspected to be contaminated with gram negative bacteria to determine the presence or absence of gram negative bacteria in the specimen sample, and which can detect the presence of gram negative bacteria without the need of performing a preliminary gram negative bacteria growth step, said medium comprising operative amounts of essential vitamins and elements to support growth of gram negative bacteria, effective amounts of antibiotic material operable to render any yeast and gram positive bacteria in the specimen sample incapable of metabolizing nutrients, and a nutrient chromogenic substrate for L-alanine aminopeptidase which is substantially the sole carbon source nutrient in the medium and which is metabolizable by gram negative bacteria to the extend needed to support continued reproductive growth thereof, and which, when metabolized, releases a chromogen which alters the color of the specimen there being no other nutrients in the medium which are able to support substantial reproductive growth of gram negative bacteria in the sample.

9. The medium of claim 8 wherein said chromogenic substrate of L-alanine aminopeptidase is an alanine selected from the group consisting of L-alanine-B-orthonitrophenyl, B-napthalamide-B-L-alanine, alpha-napthol-B-L-alanine, methylumbilliferyl-B-L-alanine and mixtures thereof.

10. A specific medium for addition to a specimen sample of a material suspected to be contaminated to determine the presence or absence of a target microbe in the specimen sample, and which can detect the presence of said target microbe without the need of performing a preliminary target microbe growth step, said medium comprising operative amounts of essential vitamins and elements needed to support growth of said target microbe and a nutrient-indicator which is the primary nutrient in the medium and which is substantially the only nutrient in said medium which can be metabolized by said target microbe to the extent needed to support continued growth thereof, and, which cannot be metabolized by other viable microbes in the specimen to that extend, said nutrient-indicator including a metabolizable moiety and a sample-altering moiety the latter of which is released only when said nutrient-indicator is metabolized by said target microbe, whereupon a sensible characteristic of the sample is altered, said medium being in the form of a non-sterile, water-soluble powder.

11. A method of testing a specimen suspected to be contaminated to determine the presence or absence of a target microbe in the specimen, said method comprising the steps of:
  (a) obtaining at least one known volume sample of the specimen;
  (b) forming a specimen sample and medium mixture by adding to the specimen sample a predetermined amount of a medium which is soluble in the specimen sample and which contains effective amounts of vitamins and elements essential to growth of the target microbe, and a nutrient-indicator which is the primary nutrient in the medium and which is the only nutrient in the medium which the target microbe can metabolize to an extent needed to support continued reproductive growth thereof, and which cannot be metabolized by other viable microbes in the specimen sample to that extend, said nutrient-indicator including a metabolizable moiety and a sample altering moiety, said sample altering moiety being operable to alter a sensible, characteristic of the specimen sample when said nutrient-indicator is metabolized by the target microbe; and
  (c) monitoring the specimen sample and medium mixture for at least about twenty hours or until said characteristic has been altered to determine the presence or absence of the target microbe.

12. The method of claim 11, wherein said medium is added to a 1.0 ml sample of the specimen, to a 0.1 ml sample of the specimen, and a 0.01 ml sample of the specimen and each specimen sample and medium mixture is monitored for characteristic alteration to verify the concentration of said target microbe in the specimen.

13. The method of claim 12 further comprising the step of incubating the specimen sample-medium mixtures at a temperature in the range of about 20° C. to about 44.5° C. during monitoring thereof.

14. The method of claim 11 further comprising the step of adding to the specimen sample an effective amount of antibiotic material for rendering any microbes, other than the target microbe, incapable of metabolizing said nutrient-indicator.

15. A specific medium for the detection of a target micro-organism in a sample, and which can detect the presence of said target micro-organism without the need of performing a preliminary target micro-organism growth step, said medium comprising a two component mixture, a first component of which includes a combination of elements, vitamins and other essential nutritive materials required to support growth of the target micro-organism but said first component being unable by itself to allow substantial reproductive growth of the target micro-organism or any other viable organism in the sample; and a second component which comprises a primary nutrient ingredient, which is present in operative amounts to allow substantial growth of only the target micro-organism, said ingredient being in the form of a coupled nutrient-indicator such that when the nutrient is metabolized by the target micro-organism, a sensible characteristic of the sample is altered there being no other nutrients in the medium which are able to support substantial reproductive growth of the target micro-organisms in the sample.

16. A specific medium for combination with a specimen sample of a material to simultaneously detect total coliforms and $E.\ coli$ in the sample, said medium comprising: operative amounts of vitamins and elements needed to support growth of total coliforms and $E.\ coli$; a first nutrient-indicator which is the primary nutrient in the medium for total coliforms and which is a nutrient which cannot be metabolized by other viable microbes in the sample to the extend needed to support continued reproductive growth thereof; and a second nutrient-indicator which is the primary nutrient in the medium for $E.\ coli$ and which is a nutrient which cannot be metabolized by other viable microbes in the sample to the extent needed to support continued reproductive growth thereof; one of said nutrient indicators, when metabolized, producing a visible color change in the specimen, and the other of said nutrient-indicators, when metabolized, producing a normally non-visible color change in the specimen which is rendered visible upon exposure of the sample to an excitation light source there being no other nutrients in the medium which are able to support substantial reproductive growth of total coliforms and $E.\ coli$ in the sample.

17. The specific medium of claim 16 wherein said first nutrient-indicator is a substrate for $\beta$-galactosidase; and said second nutrient-indicator is a substrate for $\beta$-glucuronidase.

18. A specific medium for combination with a specimen sample of a material to detect total coliforms in the sample, said medium comprising: operative amounts of vitamins and elements needed to support growth of total coliforms; and a nutrient-indicator which is the primary source of metabolizable carbon in the medium for total coliforms and which is a nutrient which cannot be metabolized by other viable microbes in the sample to the extend needed to support continued reproductive growth of said other viable microbes, said nutrient indicator, when metabolized, producing a visible color change in the specimen, and said nutrient indicator being a substrate for $\beta$-galactosidase there being no other nutrients in the medium which are able to support substantial reproductive growth of total coliforms in the sample.

19. A non-sterile, water soluble powdery specific medium for determining the presence or absence of a target microbe in a specimen sample of water suspected to be contaminated, and which can detect the presence of said without the need of performing a preliminary target microbe growth step, said medium comprising about 10% to about 50% by weight of a nitrogen-containing compound, about 0.06% to about 1.0% by weight of amino acids essential to growth of said target microbe, about 0.09% to about 0.60% by weight of vitamins essential to growth of said target microbe, about 0.05% to about 0.70% by weight of elements essential to growth of said target microbe, about 6.4% to about 85% by weight of salts essential to growth of said target microbe, and about 1.20% to about 2.0% of a nutrient-indicator which is substantially the sole carbon source nutrient in the medium and which is the only nutrient in said medium which can be metabolized by said target microbe to the extent needed to support continued reproductive growth thereof and which is a nutrient which cannot be metabolized by other viable microbes in the sample to that extent, said nutrient-indicator, when metabolized by said target microbe, releasing a moiety which will alter a sensible characteristic of the sample.

* * * * *

UNITED STATES PATENT AND TRADEMARK OFFICE
CERTIFICATE OF CORRECTION

PATENT NO. : 4,925,789

DATED : May 15, 1990

INVENTOR(S) : Stephen C. Edberg

It is certified that error appears in the above-identified patent and that said Letters Patent is hereby corrected as shown below:

In Column 5, line 12, delete the word "taxomonic" and insert the word --taxonomic-- in lieu thereof.

In Column 11, line 12, delete the word "or" and insert the word --of-- in lieu thereof.

Same Column, line 26, after "p" insert -- - --.

Same Column, Claim 1, line 41, delete the word "of" and insert the word --or-- in lieu thereof.

In Column 12, Claim 4, line 11, delete the word "extend" and insert the word --extent-- in lieu thereof.

Same Column, Claim 5, line 18, delete the word "of" and insert the word --for-- in lieu thereof.

Same Column, Claim 8, line 46, delete the word "extend" and insert the word --extent-- in lieu thereof.

Same Column, Claim 9, line 54, delete the word "of" and insert the word --for-- in lieu thereof.

In Column 13, Claim 10, line 5, delete the word "extend" and insert the word --extent-- in lieu thereof.

Same Column, Claim 11, line 29, delete the word "extend" and insert the word --extent in lieu thereof.

In Column 14, Claim 16, line 17, delete the word "extend" and insert the word --extent-- in lieu thereof.

UNITED STATES PATENT AND TRADEMARK OFFICE
CERTIFICATE OF CORRECTION

PATENT NO. : 4,925,789

DATED : May 15, 1990

INVENTOR(S) : Stephen C. Edberg

It is certified that error appears in the above-identified patent and that said Letters Patent is hereby corrected as shown below:

In Column 14, Claim 18, line 44, delete the word "extend" and insert the word --extent-- in lieu thereof.

Same Column, Claim 19, line 56, after the word "said" insert --target microbe--.

Signed and Sealed this

Twenty-ninth Day of June, 1993

Attest:

MICHAEL K. KIRK

Attesting Officer

Acting Commissioner of Patents and Trademarks